US00PP12399P2

(12) United States Plant Patent
Hanes

(10) Patent No.: US PP12,399 P2
(45) Date of Patent: Feb. 12, 2002

(54) GERANIUM PLANT NAMED 'AMRI CHERRY ROSE'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/335,186

(22) Filed: Jun. 17, 1999

(51) Int. Cl.[7] ..... A01H 5/00
(52) U.S. Cl. ..... Plt./329
(58) Field of Search ..... Plt./329, 324, 325, Plt./327, 328

(56) References Cited

U.S. PATENT DOCUMENTS

PP10,961 P * 6/1999 Hanes ..... Plt./329

OTHER PUBLICATIONS

GTITM UPOV ROM Citation for 'Amri Cherry Rose' as per CA PBR 98–1459; Aug. 21, 1998.*

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A new and distinct geranium plant named 'Amri Cherry Rose' is provided. 'Amri Cherry Rose' is characterized by its green foliage, cherry rose colored semi-double flowers on large umbels, its fast rooting and rounded growth habit.

2 Drawing Sheets

BACKGROUND OF THE NEW PLANT

The present invention comprises a new and distinct geranium plant, botanically known as *Pelargonium hortorum* Bailey, and hereinafter referred to by the name of 'Amri Cherry Rose'.

This new geranium originated from a cross made by the inventor of the seed parent 4708-2(unpatented), a plant from the breeding line 4708, and the pollen parent 4274-1 (unpatented), a plant from the breeding line 4274.

'Amri Cherry Rose' is the product of a planned breeding program intended to create new geranium plants with cherry rose colored flowers, semi-double flower form, green foliage, vigorous growth and superior cutting productivity.

'Amri Cherry Rose' was created in 1996 in Gilroy, Calif., and has been repeatedly asexually reproduced by cuttings in Gilroy, Calif., and Guatemala over a 3-year period. The plant has also been trialed at Okemos, Mich. The plant has been found to retain its distinctive characteristics through successive propagations; and this novelty appears to be firmly fixed and reproduces true to type.

DESCRIPTION OF THE DRAWING

This new geranium plant is illustrated by the accompanying photographic drawings which shows blooms, buds, and foliage of the plant in full color, the colors shown being as true as can be reasonably obtained by conventional photographic procedures.

DESCRIPTION OF THE NEW CULTIVAR

Figure 1:
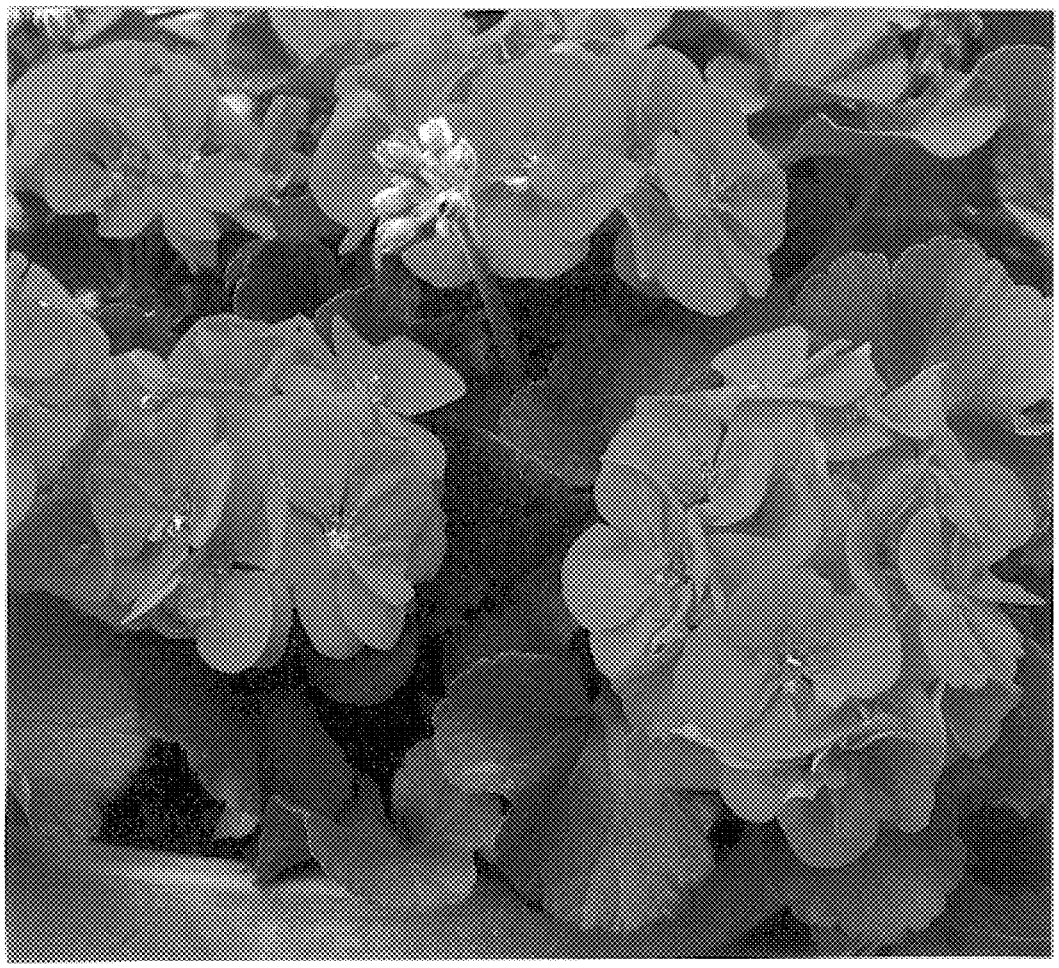
FIG. 1 shows the blooms, buds and foliage of the plant.
Figure 2:
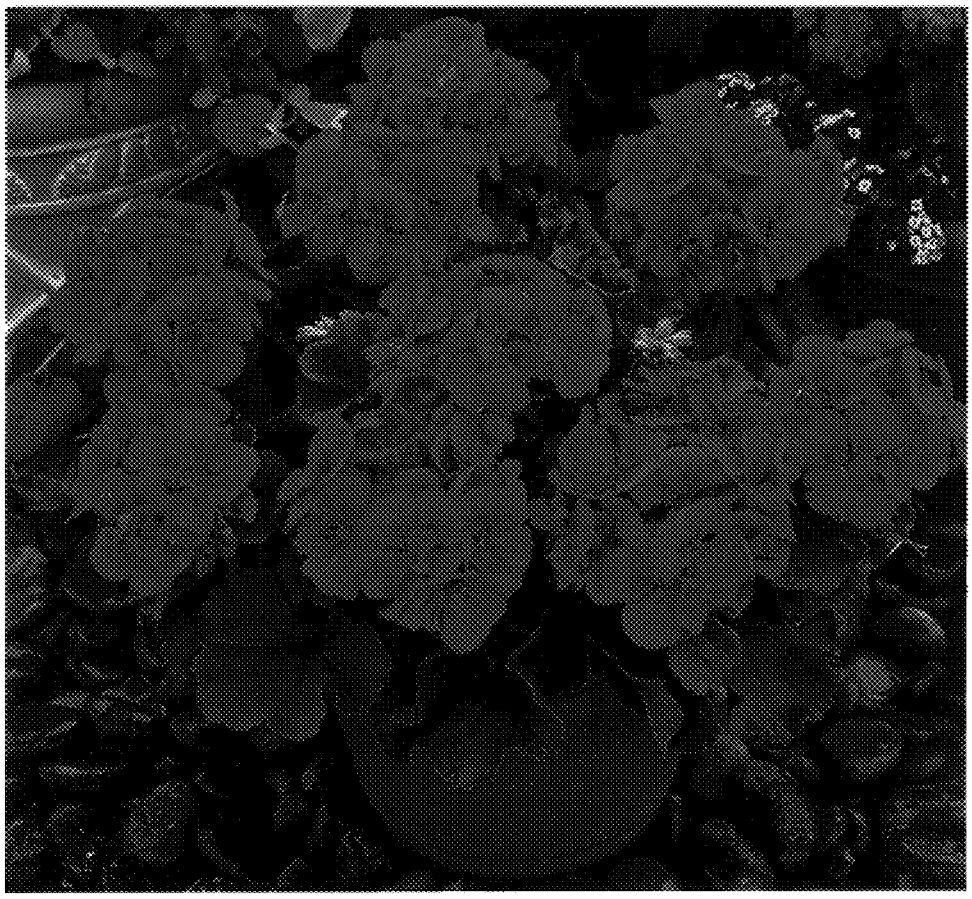
FIG. 2 shows the overall plant habit.

The following detailed descriptions set forth the distinctive characteristics of 'Amri Cherry Rose'. The data which defines these characteristics were collected from asexual reproductions carried out in Gilroy, Calif. The plant history was taken on 14-week old plants, blossomed under natural light in a greenhouse and color readings were taken in the greenhouse in Gilroy, Calif., under ambient light. Color references are primarily to The R.H.S. Colour Chart of The Royal Horticultural Society of London (R.H.S.).

The Plant

Classification:
*Botanical.*—*Pelargonium hortorum* Bailey.
*Commercial.*—*Zonal geranium.*

Form: Round growth habit.

Height: 12 cm., in a 4-inch pot plant, excluding blooms; plant height from soil level to top of umbels is 17.0–18.3 cm; width is 21–23 cm.

Growth: Vigorous, good basal branching, withstands multiple harvests of cuttings, produces a commercially acceptable size flowering plant in a 4 inch pot within 12 weeks and produces a strong, weather resistant plant in outdoor field trials in several different climate zones.

Plant habit: Good plant habit and good shipping quality as rooted or unrooted cuttings.

Time to produce a finished flowering plant: 12 weeks.

Outdoor plant performance: The plant exhibits good heat tolerance and strong growth, with a rounded growth habit.

Leaves

Quantity: Abundant.

Size: Diameter approximately 7.5 cm; Length is 3.6–4.2 cm; Apex is obtuse; Base is cordate.

Shape: Rounded cordate with occasional upfolding between veins.

Margin: Irregularly crenate.

Texture: Leathery and pubescent on both surfaces, especially along veins.

Ribs and veins: Distinctly palmate, 3.7 to 4.7 cm. long.

Color: Upper side: Green color darker than RHS 144A and greener than RHS 146A; Under side: Green color RHS 144A; Ribs and veins are green RHS 144B.

Petioles: Approximately 5.0 to 6.5 cm in length; 3 mm in diameter; color is yellow-green R.H.S. 144A.

Lateral branches: Length is 3.5–4.0 cm; Internode is 1.0–1.5 cm; Color is yellow-green RHS 144C.

Roots: Time to initiate roots is 7–10 days; time to develop roots is 3–4 weeks; description is fibrous yet coarse, white, slightly hairy.

The Bud

Size:

*Diameter.*—Approximately 6 mm.

*Length.*—Approximately 1.5 cm. to 2.0 cm. at time of bud opening.

Shape: Pointed ovoid.

Color: Petals when sepals first divide, 57C RHS.

Sepals: 5 in number Length is 1 cm; Width is 3 mm; Apex is aristate/cuspidate; Base is truncate; flat behind petals; Pointed linear lanceolate; Upper and Lower color is green, 146D RHS, in an open flower.

The Flower

Flowering season: Continuous throughout the year.

Size: Approximately 4.6 cm. diameter, 0.5 cm. deep.

Form: Cup-shaped semi-double flowers when bloom first opens, later flattening with maturity.

Petals/Petaloids: Six imbricate petals, obovate shaped, obtuse apex, attenuate base and entire undulated margins. Two to three petaloids of varying shape. Both petals and petaloids upper surface color is red, RHS 57B and lower surface of petals and petaloids is red RHS 57C. Petal and petaloid color change is minimal with age. Both petal and petaloid upper surface fades to lighter than but close to RHS 57B and lower surface of petals and petaloids fades to lighter than but close to RHS 57C. Petals and petaloids soft and satiny.

Pedicel: Approximately 2.4 cm. in length; yellow-green RHS 144B with an overlay of red-purple RHS 59B.

Persistence: An open flower will hold its petals until the flower begins to dehisce, or approximately 7–10 days.

Inflorescence

Type: An umbel composed of approximately 27 flowers, erect or laterally ascending; diameter is 9.5–10.0 cm; depth is 4.0 cm from bottom of pedicel to top of umbel.

Peduncle: Approximately 9–12 cm. in length, green, RHS 144A, in color

Reproductive Organs

Stamens:

*Anthers.*—6–8 positioned below the mature stigma, dull red RHS 50B prior to anthesis.

*Filaments.*—White near base and mid length, graduating to dull red, RHS 61C, near anther.

*Pollen.*—Copious amount; Orange, between RHS 34A and 34B, in color.

Pistil:

*Number.*—1.

*Length.*—Approximately 7 mm.

*Stigma.*—5 linear lobes of near equal length, curling back toward ovary, purplish-red RHS 53B.

*Style.*—Length: Approximately 3–4 mm., color: purplish red RHS 53A.

*Ovaries.*—At anthesis, densely pubescent with white hairs, oblong. Green drying to a light brown at maturity.

Fruit/seeds: Partially fertile; maximum of five seeds per seed spike; seed length is approximately 4 mm; width is 1 mm; color is grey-orange RHS 177B but may darken with age.

Disease/Insect Resistance

No known susceptibility or resistance to typical diseases and insects of geraniums.

Comparison with Parental Cultivars

'Amri Cherry Rose' has a more red-rose flower color than parental cultivar 4708-2 which has a blue-rose flower color. Additionally, 4708-2 has darker green foliage than 'Amri Cherry Rose'. When compared to parental cultivar 4274-1, 'Amri Cherry Rose' has a more basal branched plant habit and is more floriferous than the parental cultivar.

I claim:

1. A new and distinct geranium plant substantially as herein shown and described named 'Amri Cherry Rose', that is characterized by its green foliage, cherry rose colored semi-double flowers on large umbels, its fast rooting and rounded growth habit.

* * * * *